United States Patent [19]

Teisseire

[11] 4,117,245

[45] Sep. 26, 1978

[54] PROCESS FOR THE PRODUCTION OF NORPATCHOULENOL

[76] Inventor: Paul José Teisseire, 14 avenue Pierre Sémard, Grasse, France

[21] Appl. No.: 767,461

[22] Filed: Feb. 10, 1977

Related U.S. Application Data

[62] Division of Ser. No. 594,335, Jul. 9, 1975, Pat. No. 4,055,594.

[30] Foreign Application Priority Data

Aug. 2, 1974 [CH] Switzerland .................. 10676/74
Apr. 9, 1975 [CH] Switzerland .................. 4602/75

[51] Int. Cl.² ............................................ C07C 29/00
[52] U.S. Cl. .................................................. 568/817
[58] Field of Search ............. 260/631.5, 617 F, 617 R

[56] References Cited

PUBLICATIONS

Fieser, et al., "Reagents for Organic Synthesis", vol. 2 (1969), pp. 235, 236.

Primary Examiner—Joseph E. Evans
Attorney, Agent, or Firm—Wallenstein, Spangenberg, Hattis & Strampel

[57] ABSTRACT

A novel process for the production of the valuable perfume material norpatchoulenol is disclosed which involves oxidatively decarboxylating an acid precursor according to the following reaction scheme:

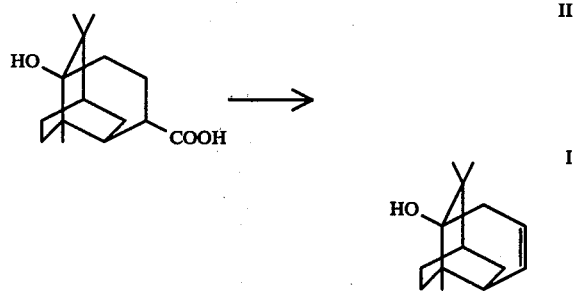

8 Claims, No Drawings

PROCESS FOR THE PRODUCTION OF NORPATCHOULENOL

This is a division of application Ser. No. 594,335, filed July 9, 1975.

DISCUSSION OF THE PRIOR ART

Norpatchoulenol is a known compound described, for example, in French Patent published under the No. 2,152,522 (filed Sept. 1, 1971). Norpatchoulenol is an extremely important odorant compound which is present in the naturally occuring Patchouli Oil. It only occurs therein at a concentration which is considerably less than that of patchoulol which latter although it is the principal constituent of Patchouli Oil is practically inodorous. The ratio of the concentrations of the two alcohols in Patchouli Oil is of the order of 1:100.

Synthetic methods for the production of norpatchoulenol and key intermediates for its production are disclosed and claimed in the German patent applications published under the Nos. 2,407,782 and 2,407,781.

OBJECT OF THE PRESENT INVENTION

It is an object of the present invention to provide additional advantageous routes to norpatchoulenol.

DETAILED DESCRIPTION OF THE INVENTION

This invention is concerned with a process for the production of norpatchoulenol having the formula

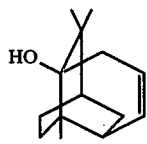

The process according to the present invention comprises oxidatively decarboxylating the acid-alcohol having the formula

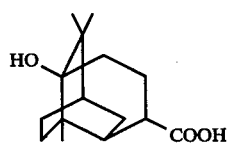

This oxidative decarboxylation may conveniently be effected with the aid of lead tetraacetate. The reaction may be effected by working in an inert organic solvent or in a polar coordinating solvent. Solvents which may be used include e.g. benzene, chlorobenzene, chloroform, dimethylformamide, tetrahydrofuran, acetonitrile, dioxane, dimethyl sulphoxide and pyridine. The rate at which the reaction proceeds depends on the nature of the solvent and the temperature of the reaction. In general, the reaction should be carried out at the lowest temperature possible in order to avoid side-reactions, including reactions such as further oxidation of the norpatchoulenol produced. The reaction temperature employed may thus vary from the ambient temperature, or even lower, up to the reflux temperature of the reaction mixture.

The reaction may conveniently be effected in the presence of catalytic amounts of cupric acetate. This reaction may further be catalysed by a variety of bases such as pyridine, as well as by salts such as lithium acetate.

The acid-alcohol starting material of formula II used in the reaction may be prepared by oxidation of the methyl group in position 4 of patchoulol which has the formula

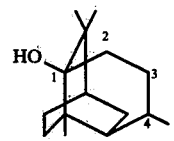

This oxidation may be effected by any convenient method, e.g. either by purely chemical means or by a biological process. One particularly interesting biological method for oxidising patchoulol consists of administering patchoulol orally either to rabbits, dogs or rats, which metabolise patchoulol in a practically quantitative yield into a mixture of the acid-alcohol of formula II and the glycol of formula

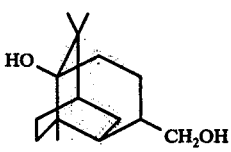

Another process for the preparation of the acid-alcohol starting material of formula II utilises the hydroxy-aldehyde of formula

The latter can be prepared by careful oxidation of the glycol IV, for example by the use of chromic acid in pyridine. The oxidation of the hydroxy-aldehyde of formula V to the acid-alcohol of formula II can be effected by any convenient method for example by moist silver oxide (formed in situ from a solution of silver nitrate and ammonium hydroxide).

A certain minor proportion of the hydroxy-aldehyde of formula V is also formed during the above mentioned biological oxidation of patchoulol in rabbits, dogs or rats.

The various intermediate compounds having the formula

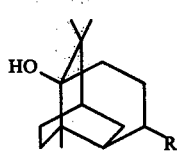

wherein R represents —COOH, —CH$_2$OH or —CHO, formed in the processes described above are novel, namely the compounds of the formulae II, IV and V.

The invention with now be illustrated with reference to the following Examples.

EXAMPLE 1

To a solution of 500 mg of the acid-alcohol of formula II, 200 mg of cupric acetate and 1 ml of pyridine in 50 ml of benzene, there are added 800 mg of lead tetraacetate. The mixture is then heated under reflux for 30 minutes. After cooling, 1,2-propanediol is added and the mixture is extracted with ethyl ether. Evaporation of the solvent yields an oil which is chromatographed on SiO₂; there are thus obtained 300 mg of a product which by comparison of thin layer chromatograms. I.R. and NMR spectra and melting points was shown to be identical to natural norpatchoulenol.

The acid-alcohol II employed may be prepared as follows:

36 hours before administration of the patchoulol, rabbits are put into the metabolism cages. They are left to fast for 24 hours before force feeding. Each rabbit (albino, about 3 kg) receives 1 g (or 1.5 g or 2 g according to trial) of patchoulol in suspension in 20 ml of 1% carboxymethylcellulose solution, then 25 ml of water. These liquid administrations are made by gastric force feeding of the rabbit anaesthetised with Nembutal (about 30 mg/kg). After the force feeding, the rabbits were allowed to partake freely of water and food. All urine passed was collected every 24 hours.

The urine collected over a period of 96 hours is acidified to pH = 4.5 with a solution of 10% HCl. There are added thereto 6 ml of (β D-glucuronide)glucuronidase (Suc d'Helix Pomatia de l'Industrie Biologique francaise). The solution is left at 37° for 24 hours, then acidified to pH = 1. After saturating the solution with NaCl, it is extracted with ethyl ether.

Evaporation of the ethyl ether yields a viscous liquid, which is immediately chromatographed on SiO₂. There are obtained 20 to 40% of the acid-alcohol of formula II and 10 to 30% of the glycol of formula IV with 50% ethyl ether, 50% petroleum ether as eluant.

Acid-alcohol of formula II:

I.R. $\nu_{c=o}$ 1700 cm⁻¹
N.M.R.

0.9 ppm (s, 3H) and 1.1 ppm (s, 6H)

Methyl ester of the acid-alcohol II:

I.R. $\nu_{OH}$= 3600 and 3500 cm⁻¹, $\nu_{c=o}$ 1725 cm⁻¹
N.M.R.

0.9 ppm (s, 3H), 1.10 ppm (s, 3H) and 1.13 ppm (s, 3H),

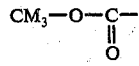

3.65 pm (s, 3H)

Glycol of formula IV:

M.P. = 104°–105° C. $(\alpha)_D^{CHCl_3} = -120°$

I.R. $\nu_{OH}$ = 3620 and 3450 cm⁻¹
N.M.R.

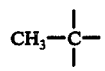

0.85 ppm (s, 3H) and 1.1 ppm (s, 6H)

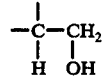

3.45 ppm (d, J=7.5 Hz, 2H)

Monoacetate of the glycol:

I.R. $\nu_{OH}$ = 3600 and 3500 cm⁻¹, $\nu_{c=o}$ 1725 cm⁻¹
N.M.R.

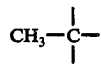

0.85 ppm (s, 3H) and 1.1 ppm (s, 6H)

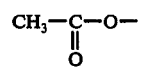

2.05 ppm (s, 3H),

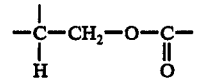

3.90 pm (d, J=7.5 Hz, 2H).

EXAMPLE 2

3 g of a chromic anhydride-pyridine complex are dissolved in 50 ml of methylene chloride to which 6 drops of pyridine have been added. A solution of 460 mg of the glycol of formula IV dissolved in 10 ml of methylene chloride is then added and the reaction mixture is agitated for 4 hours at the ambient temperature. The reaction mixture is then filtered and the precipitate is washed with 50 ml of methylene chloride. The combined filtrates are then washed successively four times with 10 ml of 5% aqueous sodium hydroxide, three times with 10 ml of 10% aqueous hydrochloric acid, twice with 10 ml of saturated aqueous sodium bicarbonate and finally twice with 10 ml of water. The organic solution is then dried over sodium sulfate and filtered. The solvent is distilled off. There is obtained 465 mg of the hydroxy-aldehyde of formula V which is purified on a silica column. The pure hydroxy-aldehyde has the following characteristics:

$[\alpha_D]^{CHCl_3} = -40°$; IR: $\nu_{OH}$ at 3500 cm⁻¹, $\nu_{C=O}$ at 1715 cm⁻¹;

NMR:

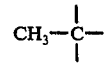

singlet (3H) at 0.89 ppm;

2 singlets coinciding (6H) at 1.08 ppm;

CHO singlet (1H) at 9.64 ppm.

EXAMPLE 3

To a solution of 440 mg of silver nitrate in 1 ml of water there is added, with stirring, a solution of 200 mg of sodium hydroxide in 1 ml of water, then a solution of 146 mg of the hydroxy-aldehyde of formula V in 0.5 ml of pentane. Stirring is continued at ambient temperature for 30 minutes and the mixture is then heated to 40° C. for 2 hours. After cooling the mixture is filtered and the precipitate is washed with 10 ml of hot water. The combined filtrates are extracted twice with 5 ml of ethyl ether and then acidified with aqueous 36% w/w hydrochloric acid. Sodium chloride is then added until a saturated solution is obtained. The solution is then extracted three times with 10 ml of diethyl ether. The combined ethereal phases are washed with saturated aqueous sodium chloride and then dried over sodium sulfate. One obtains 110 mg of the acid alcohol of formula II having the following physical characteristics:

$[\alpha_D]^{CHCl_3} = -87°$; IR: $\nu_{CO}$ at 1700 cm$^{-1}$, $\nu_{OH}$ at 3180 and 2600 cm$^{-1}$, $\nu_{OH}$ at 3480 cm$^{-1}$; NMR:

singlet (3H) at 0.88 ppm;

singlet (3H) at 1.08 ppm;

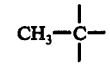

singlet (3H) at 1.11 ppm.

What is claimed is:

1. A process for the preparation of norpatchoulenol having the formula

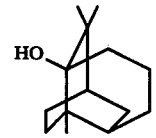

I which comprises oxidising patchoulol and then oxidatively decarboxylating the resulting acid of the formula

II

2. A process according to claim 1, wherein lead tetraacetate is employed as the oxidative decarboxylation agent.

3. A process according to claim 2, wherein cupric acetate is utilised as catalyst.

4. A process according to claim 2, wherein the reaction is effected in the presence of a base.

5. A process according to claim 1, wherein the oxidation of patchoulol is effected biologically.

6. The process of claim 1, in which the oxidative decarboxylation reaction is carried out in an organic solvent and at a temperature in a range up to the reflux temperature of the reaction mixture.

7. A process according to claim 4, in which the oxidation decarboxylation reaction is carried out in an organic solvent and at a temperature in a range up to the reflux temperature of the reaction mixture.

8. A process according to claim 5, in which patchoulol is force fed to rabbits, dogs or rats, urine is collected from said animals and the acid-alcohol of formula II is recovered from said urine.

* * * * *

UNITED STATES PATENT AND TRADEMARK OFFICE
CERTIFICATE OF CORRECTION

PATENT NO. : 4,117,245
DATED : September 26, 1978
INVENTOR(S) : Paul José Teisseire It is certified that error appears in the above-identified patent and that said Letters Patent are hereby corrected as shown below:

Column 6, claim 1, the formula should read as shown below.

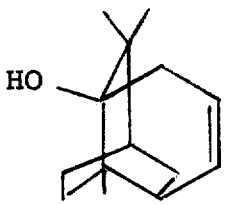

Signed and Sealed this

Third Day of April 1979

[SEAL]

Attest:

RUTH C. MASON
Attesting Officer

DONALD W. BANNER
Commissioner of Patents and Trademarks